(12) United States Patent
Tammishetti et al.

(10) Patent No.: US 10,197,544 B2
(45) Date of Patent: Feb. 5, 2019

(54) PORTABLE TEST-DEVICE FOR SELECTIVE FLOCCULATION

(71) Applicant: Tata Consultancy Services Limited, Mumbai (IN)

(72) Inventors: Venugopal Tammishetti, Pune (IN); Dharmendr Kumar, Pune (IN); Beena Rai, Pune (IN); Pradip, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 125 days.

(21) Appl. No.: 15/467,911

(22) Filed: Mar. 23, 2017

(65) Prior Publication Data

US 2017/0276661 A1    Sep. 28, 2017

(30) Foreign Application Priority Data

Mar. 23, 2016  (IN) .............................. 201621010151

(51) Int. Cl.
| | | |
|---|---|---|
| *G01N 1/00* | (2006.01) |
| *G01N 33/24* | (2006.01) |
| *B01F 5/06* | (2006.01) |
| *B01F 13/10* | (2006.01) |
| *B03D 3/06* | (2006.01) |

(52) U.S. Cl.
CPC ........... *G01N 33/24* (2013.01); *B01F 5/0602* (2013.01); *B01F 13/1016* (2013.01); *B03D 3/06* (2013.01); *B01F 2215/0083* (2013.01); *B03D 2201/002* (2013.01); *B03D 2201/007* (2013.01)

(58) Field of Classification Search
CPC ....................................................... G01N 1/00
See application file for complete search history.

(56) References Cited

U.S. PATENT DOCUMENTS 4,274,945 A    6/1981  Goodman et al.

FOREIGN PATENT DOCUMENTS

| JP | 2010-259991 | 11/2010 |
| WO | WO 2007/115531 A1 | 10/2007 |

*Primary Examiner* — Jyoti Nagpaul
(74) *Attorney, Agent, or Firm* — Finnegan, Henderson, Farabow, Garrett & Dunner LLP

(57) ABSTRACT

This disclosure relates generally to selective flocculation, and more particularly to portable test-device for performing selective flocculation experiments in continuous mode. The test-device includes a slurry inflow system, a flocculant tank, a static mixer, a control pumping system, and a thickener system. The static mixer is connected to the slurry inflow system and the flocculant tank, to receive and mix flocculant solution and slurry and cause formation of floc. The control pumping system connects the flocculant tank and the slurry inflow system to the static mixer to control the control parameters responsible for pumping the slurry and flocculant solution in the continuous mode in the static mixer. The thickener system comprises a thickener tank to receive treated slurry and the floc from the static mixer, separately collect tailings and the floc from the thickening tank. The components of the portable test-device are removably connected to each other.

6 Claims, 1 Drawing Sheet

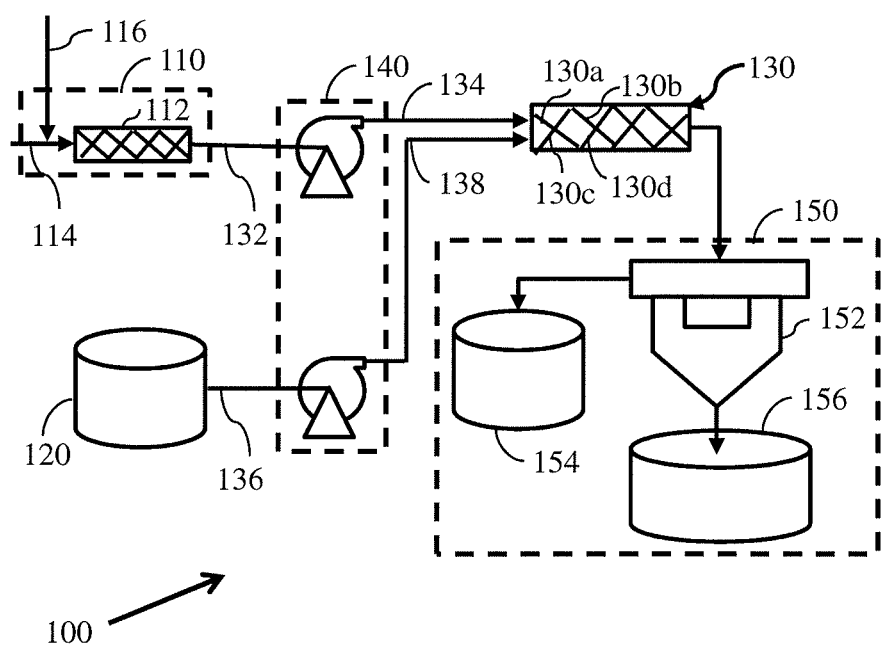

PORTABLE TEST-DEVICE FOR SELECTIVE FLOCCULATION

PRIORITY CLAIM

This U.S. patent application claims priority under 35 U.S.C. § 119 to: India Application No. 201621010151, filed on 23 Mar. 2016. The entire contents of the aforementioned application are incorporated herein by reference.

TECHNICAL FIELD

This disclosure relates generally to slurry treatment apparatus, and more particularly to a portable test-device for selective flocculation slurry in continuous mode.

BACKGROUND

Modern researches are focused on slurry beneficiation processes. Slurry beneficiation involves mineral processing in which gangue minerals are separated from ore to produce high grade material. Various methods allow to beneficiate grade slurry/ores. These methods involve processing of raw slurry in large apparatuses that can be installed at plant site. The processing of raw slurry at the plant site allows for beneficiation in a continuous mode. Alternatively, the beneficiation can be performed in a laboratory, in which case, a large quantity of raw slime has to be carried to the laboratory to conduct experiments.

The above methods of beneficiation have various limitations. For example, the processing of raw slurry in large apparatuses at the plant site requires installation of huge machinery which is a cost inefficient solution. Also, for performing beneficiation in the laboratory setup, since large quantity of raw slime has to be carried to the laboratory, the process becomes cumbersome

SUMMARY

Embodiments of the present disclosure present technological improvements as solutions to one or more of the above-mentioned technical problems recognized by the inventors in conventional systems. For example, in one embodiment a portable test-device is provided for performing selective flocculation experiments in continuous mode. The test-device includes a slurry inflow system, a flocculant tank, a second static mixer, a control pumping system, and a thickener system. The slurry inflow system is adapted to receive slurry. The slurry inflow system includes a first static mixer capable of being removably connected to slurry pipes capable of carrying slurry from a plant. The flocculant tank is capable of storing a flocculant solution. The flocculant solution is capable of causing formation of floc when mixed with the slurry. The second static mixer is removably connected to the first static mixer and the flocculant tank, and is capable of in-line mixing the flocculant solution and the slurry, to cause formation of the floc and tailings. The second static mixer includes a plurality of mixing elements configured to divide and rotate a fluid, where the fluid includes the flocculant solution and the slurry in a plurality of flow-directions. The second static mixer is adapted to minimize dead zones encountered in the mixing of the flocculant solution and the slurry. The control pumping system is removably connects the flocculant tank and the first static mixer to the second static mixer. The control pumping system is configured to control one or more control parameters responsible for pumping the slurry and flocculant solution in the continuous mode. The thickener system is removably connected to the second static mixer. The thickener system includes a thickener overflow tank to collect the tailings and a thickener underflow tank to collect the floc.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 1 is a block diagram illustrating a portable test-device for testing slurry in continuous flocculation mode, in accordance with an example embodiment.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Some embodiments of this invention, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any devices and methods similar or equivalent to those described herein can be used in the practice or testing of embodiments of the present invention, the preferred devices and methods are now described.

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Typically, for performing selective flocculation experiments, huge amounts of sample of slurry is collected, and brought to laboratory where the sample is homogenized to make it representative, and further for performing experiments. However, the process of sample collection, bringing the sample from the plant, and homogenizing is time consuming. Additionally, performing selective flocculation experiments on commercial scale thickeners may not be advisable due to the consumption of huge amounts of slurry and reagents in testing stage itself, thereby increasing the overall costs associated with the experiment.

Various embodiments disclosed herein provide device to conduct selective dispersion-flocculation experiments in a manner that overcomes limitations of existing methods and devises used for said experiments. For example, the embodiments disclose method and device for conducting selective flocculation experiments in a cost efficient and time-efficient manner. The disclosed system can be implemented in form of a test device such that the test device is easy to carry to places such as beneficiation plants, research lab, and so on to perform experiments. Moreover, the disclosed system reduces the space required for the flocculation set-up.

While aspects of described methods and systems for selective flocculation can be implemented in any number of different systems, utility environments, and/or configurations, the embodiments are described in the context of the following exemplary system(s).

FIG. 1 illustrates a portable test-device 100, in accordance with an example embodiment. For the brevity of description, the portable test-device 100 may be referred to as the test-device 100 hereinafter. The test-device 100 can be utilized for flocculation of slime samples such as iron ore, copper ore, and the like. The test-device 100 is shown to include a slurry inflow system 110, a flocculant tank 120, a second static mixer 130, a control system 140, and a thickener system 150.

The slurry inflow system 110 receives slurry feed from the plant. In an embodiment, the slurry inflow system is also configured to perform pH conditioning of the slurry. In an embodiment, the pH conditioning of the slurry or slime sample is performed since during beneficiation, for a given dispersant-flocculent combination, an optimum pH has to be maintained for best separation and maximum recovery of ore from the slurry or slimes. In an embodiment, the density of the slurry may be controlled in the slurry inflow system 110. The density of the slurry may be controlled by addition or removal of water to the slurry. Addition of water decreases the density of slurry pulp. In an embodiment, the addition of water may be done in flow before or during the pH conditioning. Also, removal of water increases the density of slurry pulp. In an embodiment, the removal of water from the slurry can be performed by filtration. In an embodiment, the pH of the slurry may be controlled by controlling a flow of the pH conditioner to the slurry inflow system 110.

In an embodiment, the slurry inflow system 110 includes a first static mixer 112 that is capable of directly receiving the plant slurry stream (as indicated by 114) and the pH conditioner (as indicated by 116) from an external pH conditioner tank connected to the first static mixer 112. The first static mixer 110 mixes the slurry received directly from the plant slurry stream with the pH conditioner, to obtain pH treated slurry. The pH treated slurry can then be provided to the mixing unit 130 through the control pumping system 140.

The flocculation tank 120 is adapted to store a flocculation solution. The flocculation solution is utilized for treating slurry. The flocculation solution facilitates in agglomerating particulates that can then settle from the slurry. The flocculation solution can be mixed with the slurry for the purpose of treating the slurry to form flocculants (or flocs), such as clay, claylike waste, metal oxide particulate wastes, and so on. Herein, the slurry can be pH treated slurry. For selective separation of iron ores, alkaline pH can be utilized.

The second static mixer 130 is removably connected to the slurry inflow system 110 and the flocculant tank 120. In an embodiment, the second static mixer 130 is removably connected to the slurry inflow system 110 and the flocculant tank 120 by a fastening mechanism, for example, by using clamps, adhesive fasteners, and the like. The second static mixer 130 is connected to the slurry inflow system 110 and the flocculation tank 110 through the conduit pipes, such as pipes 132, via the control system 140. The second static mixer 130 receives the slurry from the slurry inflow system 110 through the conduit pipe 134. Also, the second static mixer 130 is connected to the flocculation tank 120 through pipe, such as pipe 136. Further, second static mixer 130 receives the flocculation solution from the flocculation tank 120 through the conduit pipes 138, via the control system 140. The flocculant solution is added to the slime (or slurry) stream in the second static mixer 130 to enable inline (or continuous) mixing of the flocculant solution with the slime (or slurry). In an embodiment, the second static mixer 130 is installed inline (along the flow pipe). The dimensions (length) of the static mixer can be in a range of 15-50 cm.

The second static mixer 130 includes multiple mixing elements (for example, elements 130a, 130b, 130c, 130d and so on) having walls throughout the length thereof. The mixing elements 130a-130d are configured to divide and rotate a fluid having the flocculant solution and the slurry in a plurality of flow-directions. For example, when fluid having the mixture of slurry and flocculant solution is made to pass through the second static mixer, the walls of the static mixer along with the mixing elements 130a-130d cause the fluid to move radial to the diameter of the second static mixer 130. As the stream of mixture passes over mixing element, the mixing elements induce mixing together of the flocculant solution and the slurry. Particularly, the stream is split into halves and layers of streams. The static mixer accomplishes the mixing of the slurry with the flocculant solution through extreme turbulence in the flow. It will be noted that herein the second static mixer 130 is shown to include multiple mixing elements, however, the static mixer may have different number of mixing elements than the elements shown here, for different lengths and configurations of the second static mixer. Herein, it will also be noted that due to the configuration of the mixing elements 130a-130d within the second static mixer 130, the second static mixer 130 enables in fast conditioning of the slurry. Also, the second static mixer 130 minimizes dead zones encountered in the mixing of the flocculant solution and the slurry.

The control pumping system 140 is configured to removably connect the slurry inflow system 110 and the flocculant tank 120 with the second static mixer 130 (as illustrated in FIG. 1). In an embodiment, the control pumping system 140 removable connects the flocculant tank 120 and the slurry inflow system 110 to the second static mixer 130 by fastening mechanisms such as clamps, adhesive fasteners, and the like. The control pumping system 140 facilitates in pumping slime slurry and flocculant solutions from the slurry inflow system 110 and the flocculant tank 120, respectively to the second static mixer 130 in a controlled manner. Flow rates can be varied between 0.5 to 10 liters per minute. In an embodiment, the control pumping system 140 includes control valves. Alternatively, the control pumping system 140 may include pumps. Herein, the control pumping system 140 facilitates in varying parameters such as flowrates of the slurry and the flocculation solution, reagent dosage thereby enabling in performing the experiments to determine optimal conditions. For example, by controlling flow rates of slurry and/or flocculant solution, the control pumping solution is able to control reagent dosage. Herein, reagent dosage refers to the quantity of reagent (flocculant) added per unit of slurry/solids. The reagent dosage can be in ppm (parts per million) or g/t (grams per ton of solids). Concentration of reagent stock solution can be in between 1000 to 5000 ppm.

Once the slurry is treated with the flocculant solution, solids agglomerate to form floc. The increased size of floc facilitate faster settling thus flocculated solid particles settle faster than the smaller particles in the system. Smaller and lighter particles go into the overflow. In case of non-selective flocculation, all the particles form flocs and settle down and overflows can be cleared with water. In one implementation, the thickener system 150 is removably connected to the second static mixer 130 by fastening mechanisms such as clamps, adhesive fasteners, and the like. In one implementation, the thickener system 150 is connected to the second static mixer 130 to receive the treated slurry including tailings and the floc. The thickener system 150 facilitates in separating the floc from the tailings in the treated slurry. In one implementation, the thickener system 150 includes a thickener tank 152, a thickener overflow tank 154 and a thickener underflow tank 156. The thickener tank 152 receives the slurry treated in the second static mixer 130 and the floc from the second static mixer 130. The thickener tank 152 is connected to the thickener overflow tank 154 to collect tailings from the treated slurry, and to the thickener underflow tank 156 to collect the flocs from the thickening tank.

It will be noted that at a pilot/plant scale, the flocculation process is continuous mode where parameters such as flow-rates, mixing and reagent dosage are to be tested, involves consumption of huge amount of material. It is generally difficult to carry such large volume of slurry samples that may be required for experiments. However, the disclosed test-device 100 is designed to be a portable system that can help in conducting flocculation experiments in continuous mode. It will be appreciated that the disclosed slurry treatment system described with reference to FIG. 1 provides a portable slurry treatment test-device that can be utilized for performing flocculation experiments in continuous mode.

At pilot/plant scale flocculation process is continuous mode where parameters such as flowrates, mixing and reagent dosage are to be tested which involves in consumption of huge amount of material. The disclosed test-device enables in varying parameters such as slurry density, flocculants density, pH, reagent dosage and flow rates and perform the experiments to determine optimal conditions. In an embodiment, the flow-rate can be varied in a range of 0.5 Liters per minute to 10 Liters per minute. The test-device involves process simplicity and is easy to scale up to achieve high grade ore by performing flocculation in Continuous mode. A table illustrating values pertaining to an example flocculation of the iron ore slurry are described below.

TABLE 1

Result of selective flocculation experiment on test-device

|  | Feed | Concentrate | Overflow |
| --- | --- | --- | --- |
| Yield, % | 100 | 45.2 | 54.8 |
| Fe grade | 56.9 | 60.5 | 49.7 |
| $Al_2O_3$ | 7.9 | 4.9 | 10.8 |
| % Loss on Ignition | 10.72 | 5.47 | 9.71 |
| % Silica | 4.84 | 3.40 | 5.89 |

As is clear from the above table. 1, the disclosed test-device is a lab scale test rig where flocculation experiments can be performed in continuous mode. The test-device is implemented in form of a compact device which is easy to carry to the place wherever experiments to be performed. When large volumes of slime samples are required for experiments, the test-device can be carried to the place where slime is available and perform experimental testing instead of carrying large amounts of slurry to the lab facility where the experiments can be performed. Herein, it is pertinent to note that the test-device can be dismantled since the components such as the slurry inflow system, the flocculant tank, the second static mixer, the control pumping system, and the thickener system are removably connected. Additionally, due to said configuration (for example, connectable or removable components and preferred dimensions of the test-device), the device is portable, and hence can be taken to a plant for performing selective flocculation experiments in continuous mode.

The foregoing description of the specific implementations and embodiments will so fully reveal the general nature of the implementations and embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

It is intended that the disclosure and examples be considered as exemplary only, with a true scope and spirit of disclosed embodiments being indicated by the following claims.

What is claimed is:

1. A portable test-device for performing selective flocculation experiments in continuous mode, the test-device comprising:
　a slurry inflow system adapted to receive slurry, the slurry inflow system comprising a first static mixer capable of being removably connected to slurry pipes, the slurry pipes capable of carrying slurry from a plant;
　a flocculant tank capable of storing a flocculant solution, the flocculant solution capable of causing formation of floc when mixed with the slurry;
　a second static mixer removably connected to the first static mixer and the flocculant tank, and capable of in-line mixing the flocculant solution and the slurry, to cause formation of the floc and tailings, the second static mixer comprising a plurality of mixing elements configured to divide and rotate a fluid comprising the flocculant solution and the slurry in a plurality of flow-directions, wherein the second static mixer is adapted to minimize dead zones encountered in the mixing of the flocculant solution and the slurry;
　a control pumping system to removably connect the flocculant tank and the first static mixer to the second static mixer, the control pumping system configured to control one or more control parameters responsible for pumping the slurry and flocculant solution in the continuous mode; and
　a thickener system removably connected to the second static mixer, the thickener system having a thickener tank and capable of separating the floc from the tailings, the thickener system comprising a thickener overflow tank to collect the tailings and a thickener underflow tank to collect the floc.

2. The test-device of claim 1, wherein the first static mixer is further connected to a pH conditioning tank through at least one inlet pipe to receive pH conditioner, the first static mixer adapted to mix the pH conditioner to the fluid comprising.

3. The test-device of claim 1, wherein the control pumping system comprises at least one of control valves and pumps.

4. The test-device of claim 1, wherein length of the static mixer is in a range of 15-50 cm.

5. The test-device of claim 1, wherein the one or more control parameters comprises pH of the slurry, flowrates of the slurry and the flocculant solution, and reagent dosage.

6. The test-device of claim 5, wherein the flow-rate is varied in a range of 0.5 Liters per minute to 10 Liters per minute.

* * * * *